United States Patent
Castiglioni et al.

(10) Patent No.: US 6,297,389 B1
(45) Date of Patent: Oct. 2, 2001

(54) PROCESS FOR THE PRODUCTION OF GAMMA-BUTYROLACTONE

(75) Inventors: Gian L Castiglioni, Riccione; Carlo Fumagalli, Albano S. Alessandro, both of (IT)

(73) Assignee: Lonza S.p.A., Milan (IT)

( * ) Notice: Subject to any disclaimer, the term of this patent is extended or adjusted under 35 U.S.C. 154(b) by 0 days.

(21) Appl. No.: 09/581,947

(22) PCT Filed: Jan. 4, 1999

(86) PCT No.: PCT/EP99/00003

§ 371 Date: Jul. 20, 2000

§ 102(e) Date: Jul. 20, 2000

(87) PCT Pub. No.: WO99/35139

PCT Pub. Date: Jul. 15, 1999

(30) Foreign Application Priority Data

Jan. 9, 1998 (IT) ............................................... MI98A0021

(51) Int. Cl.[7] .................................................. C07D 307/02
(52) U.S. Cl. ............................................................. 549/295
(58) Field of Search ..................... 549/325, 295

(56) References Cited

U.S. PATENT DOCUMENTS

| | | |
|---|---|---|
| 3,065,243 | 11/1962 | Dunlop et al. . |
| 3,580,930 | 5/1971 | Miya et al. . |
| 4,105,674 | 8/1978 | De Thomas et al. . |
| 5,112,495 | 5/1992 | Bartha et al. . |
| 5,347,021 | 9/1994 | Taylor et al. . |
| 5,698,713 | 12/1997 | Lancia et al. . |

FOREIGN PATENT DOCUMENTS

| | | |
|---|---|---|
| WO 86/03189 | 6/1986 | (WO) . |
| WO 86/07358 | 12/1986 | (WO) . |
| WO 91/16132 | 10/1991 | (WO) . |

OTHER PUBLICATIONS

CA Reference 119:225800m, "Method for preparation of gamma–butyrolactone.", vol. 119, p. 997, 1993.*

CA Reference 119:225800m, "Method for preparation of gamma–butyrolactone.", Szelejewska. et. al., vol. 119, p. 997, 1993.*

Chemical Abstracts, vol. 70, No. 23, (1969), p. 283, abstract No. 77355x.

Chemical Abstract, vol. 119, No. 27, (1993), p. 997, abstract No. 225800m.

* cited by examiner

Primary Examiner—Alan L. Rotman
Assistant Examiner—Binta Robinson
(74) Attorney, Agent, or Firm—Fisher, Christen & Sabol

(57) ABSTRACT

A process for the production of gamma-butyrolactone. Starting from maleic and/or succinic anhydride the conversion takes place in the presence of a catalyst composed of copper oxide and zinc oxide.

28 Claims, No Drawings

PROCESS FOR THE PRODUCTION OF GAMMA-BUTYROLACTONE

BACKGROUND OF THE INVENTION

This application is a 371 national stage application of International Patent Application No. PCT/EP99/00003, filed on Jan. 4, 1999, which has priority benefit of Italian Patent Application No. MI98A000021, filed on Jan. 9,1998.

1. Field of the Invention

The present invention relates to a process for selective hydrogenation of maleic or succinic anhydride to gamma-butyrolactone (GBL) in the vapor phase using a catalyst comprising a mixed oxide of copper and zinc.

2. Background Art

The present invention relates to a process for selective hydrogenation of maleic or succinic anhydride to gamma-butyrolactone (GBL) in the Sapour phase using a catalyst comprising a mixed oxide of copper and zinc GBL represents an example of a small volume commodity of great industrial interest, because of its increasing demand.

The main use of GBL is as intermediate for the synthesis of solvents with lower environmental impact than chlorinated ones, like pyrrolidone and N-methylpyrrolidone. It is also the raw material for the production of N-vinilpyrrolidone, of herbicides, pharmaceuticals and rubber additives.

The first works on GBL synthesis appeared in the 1940's, due to the start up of the Reppe process from acetylene and formaldehyde to give 1,4 butanediol (BDO) and then GBL by dehydrogenation. The drawbacks of this process are connected with the fluctuating prices of the raw materials and, mainly, with the hazard and the environmental impact of the use of both acetylene and formaldehyde.

During the second half of this century, other technologies have been studied and the number of patents about GBL production processes alternative to the Reppe process constantly increased.

The availability of maleic anhydride on industrial scale led to the development of new technologies for producing GBL, tetrahydrofurane (THF) or BDO by hydrogenation of maleic anhydride or of maleic anhydride derivatives like maleic acid diesters or succinic anhydride.

The liquid phase hydrogenation of maleic anhydride to GBL has been employed in commercial production, but never reached great industrial importance.

Many patents describe the vapor phase hydrogenation of maleic anhydride or its esters, but mainly for the production of BDO; for instance, WO 86/03189 describe the vapor phase hydrogenation of diethyl maleate to BDO. WO 86/07358 describes a similar process for GBL production.

From a technological and economical point of view the esters of maleic acid or other maleic acid and/or succinic acid derivatives are less desirable raw materials compared with maleic anhydride.

Many patents describe the direct vapor phase hydrogenation of maleic anhydride to GBL, but none of the processes disclosed are completely satisfactory.

Some of these patents claim the use of copper chromites as catalysts (e.g. U.S. Pat. No. 3,065,243) but with unsatisfactory conversion and selectivity. Similar systems were claimed in U.S. Pat. No. 3,580,930 or in EP 332 140 (Cu/Zn/Cr/Al), but none of them are completely satisfactory in terns of GBL yield, productivity, by-products formation and catalyst durability. Moreover chromium containing catalysts should not be the choice because of the negative environment impact of chromium, due to the toxicity of its compounds.

The WO 91/16132 disclose a process for the GBL production from maleic anhydride using a Cu/Zn/Al catalyst calcined at 400–525° C. Such a high temperature is a drawback in terms of plant design and operation. Different catalytic systems, based on noble metal catalysts such as Cu/Pd and Cu/Pt have been described in e.g. U.S. Pat. No. 4,105,674. The cost of the noble metal is the draw back of these catalysts.

BACKGROUND OF THE INVENTION

The object of the present invention is to provide a new and environmentally friendly process for the production of GBL by vapor phase hydrogenation of maleic anhydride and/or succinic anhydride with essentially quantitative conversion of the starting material, very high selectivity and using a commercial chromium-free catalyst.

The present invention provides a process for the vapor phase hydrogenation of maleic and/or succinic anhydride to GBL over a catalyst comprising a mixed oxide of copper and zinc.

BRIEF DESCRIPTION OF THE INVENTION

The content of Copper as CuO is 50–90 wt % and Zinc as ZnO is 10–50 wt %. Preferably the mixed oxide contains 60–80 wt % CuO and 20–40% wt ZnO. The catalyst composition may further contain inert components, such as tabletting aids or inert fillers.

Preferred catalysts are commercially available e.g. from SOd Chemie, Germany. In the active state, the catalytically active oxide material may include some metallic components (like metallic copper) formed in the activation step or during the hydrogenation.

The mixed oxide catalyst is commonly subjected to an activation treatment comprising gradually increasing its temperature from room temperature to 2000–380° C., preferably from room temperature to 2500–300° C. in the presence of a hydrogen-containing gas.

The hydrogen-containing gas in the activation treatment may be a mixture of hydrogen and nitrogen. After the activation treatment the catalyst is ready for use. Activation requires a time usually varying from about 8 to 48 h, depending on reactor size and design.

The activation of the catalyst is exothermic. In case the reactor does not provide an efficient heat removal the hydrogen-containing gas must be suitably diluted or the space velocity must be increased to control exothermic peaks. Hydrogen dilution results in longer time for the exothermic phase of activation. Large adiabatic reactors usually requires the longest activation times.

During operation molten maleic anhydride or succinic anhydride or a mixture thereof is expediently vaporised in an hot hydrogen stream in a mixing section; the mixture can then be fed into the reactor packed with the above described activated catalyst. Optionally the catalyst can be packed between two layers of an essentially inert support material, possibly with the same size and shape of the catalyst. Suitable examples of essentially inert support materials include silica, alumina, silica-alumina compounds (e.g. mullite), silicon carbide, steatite and titania.

The reaction pressure is preferably between about 1 and 100 bar, more preferably between about 1 and 30 bar.

The molar ratio of hydrogen to the anhydride in the feed is between 10:1 and 300:1 and more preferably between 40:1 and 200:1. Lower hydrogen to anhydride ratios usually result in tar formation and short catalyst life, higher ratios tend to penalise the productivity of the catalyst.

The reaction temperature is preferably between about 150 and 350° C., and more preferably between 200 and 300° C.

As it is well known by those skilled in the art, temperature and pressure range in the hydrogenation reaction depend on the desired product mixture. Increasing temperature will result in the mix containing more THF, while increasing pressure will yield substantial amounts of BDO.

The following examples illustrate this invention in more detail.

EXAMPLE 1

Laboratory Scale Reactor 350 g of g of a commercial Cu/Zn catalyst, T-4322 from Suid Chemie AG (64% CuO, 23.5% ZnO), were packed in a 1 inch (2.54 cm) internal diameter tubular reactor; the resulting height of the bed was 0.7m.

The reactor was provided with an external jacket electrically heated to assure isothermicity all over the reactor length and with an axial thermowell with a movable thermocouple which was used to control and regulate the temperature in the catalyst bed.

The catalyst was activated in situ according to the following procedure: The temperature of the reactor was adjusted to 150° C. by means of the external jacket; a mixture of $H_2/N_2$ was passed over the catalyst. To avoid hot spots the activation was performed gradually: the hydrogen content was gradually increased from 0 up to 8% vol and the temperature was risen to 250° C. During the procedure the bed temperature was checked by means of the axial thermocouple. The increase of temperature and hydrogen content was controlled in order not to exceed 20–25° C. as hot spot all along the catalytic bed. After reaching 250° C. the hydrogen content in the gas stream was gradually increased up to 100%. After 5 hours at 250° C. in hydrogen, the activation was stopped. After catalyst activation a mixture of hydrogen and maleic anhydride was fed to the catalyst bed at ambient pressure. Hydrogenation conditions and performances are summarised in table 1.

The maleic anhydride (MA) conversion was complete all over the tests. The yield of GBL was constantly over 95% molar after the first 48 hours.

TABLE 1

| T.O.S. | MA feed | $H_2$/MA | T | Molar Yields (%) | | | |
|---|---|---|---|---|---|---|---|
| (h) | (g/h) | (molar ratio) | (° C.) | GBL | SA | THF | Others |
| 48 | 14 | 141 | 228 | 95,6 | 0,5 | 0,4 | 3,5 |
| 140 | 11 | 175 | 229 | 95,3 | 0,0 | 0,6 | 4,1 |
| 150 | 12 | 165 | 228 | 97,7 | 0,0 | 0,3 | 2,3 |
| 177 | 18 | 109 | 237 | 97,6 | 0,1 | 0,2 | 2,1 |
| 209 | 8 | 236 | 233 | 96,2 | 0,0 | 0,5 | 3,3 |
| 272 | 12 | 158 | 259 | 95,1 | 0,7 | 0,1 | 4,1 |

GBL = γ-butyrolactone;
SA = succinic anhydride;
THF = tetrahydrofuran:
Others = mainly $C_2$–$C_4$ alcohols and acids.
T.O.S. = Time on Stream

EXAMPLE 2

Pilot Reactor

A tubular reactor with an internal diameter of 1 inch (2.54 cm) was packed with 1700 g of the same catalyst described in example 1 the resulting height of the bed was 3 m.

The reactor was provided with an external jacket with a circulation of diathermic oil and was equipped with an axial thermowell and a multipoint thermocouple. The catalyst was in-situ activated following the same procedure described in example 1.

After catalyst activation a mixture of hydrogen and maleic anhydride was fed to the catalyst bed at a pressure of 5 bar. Hydrogenation conditions and performances are summarized in table 2.

The MA conversion was complete all over the tests. The yield of GBL was always over 92% molar and after the first 300 hours has constantly been over 95% molar.

TABLE 2

| T.O.S. | MA feed | $H_2$/MA | T | Molar Yields (%) | | | |
|---|---|---|---|---|---|---|---|
| (h) | (g/h) | (molar ratio) | (° C.) | GBL | SA | THF | Others |
| 28 | 118 | 136 | 234 | 92,6 | 1,2 | 4,0 | 2,2 |
| 158 | 126 | 126 | 235 | 93,0 | 2,0 | 3,0 | 1,8 |
| 272 | 137 | 102 | 239 | 94,1 | 0,5 | 3,2 | 2,1 |
| 372 | 157 | 102 | 245 | 96,5 | 0,1 | 1,3 | 2,2 |
| 539 | 170 | 94 | 248 | 95,5 | 0,1 | 2,3 | 1,7 |
| 645 | 208 | 70 | 270 | 94,9 | 0,6 | 1,8 | 3,3 |
| 692 | 219 | 67 | 270 | 95,5 | 0,3 | 1,3 | 3,0 |
| 765 | 222 | 61 | 264 | 96,6 | 0,4 | 1,0 | 1,8 |

GBL = γ-butyrolactone;
SA = succinic anhydride;
THF = tetrahydrofuran:
Others = mainly $C_2$–$C_4$ alcohols and acids.
T.O.S = Time on Stream

What is claimed is:

1. A process for the production of gamma-butyrolactone consisting essentially of catalytically hydrogenating at least one member selected from the group consisting of maleic anhydride and succinic anhydride, in a vaporous mixture with a hydrogen containing gas with a catalytically active oxide material comprising a mixed oxide of 50 to 90 weight percent of copper oxide and 10 to 50 weight percent of zinc oxide, with the proviso that aluminum oxide is excluded from said catalytically active oxide material.

2. The Process according to claim 1 wherein said mixed oxide consisting of 60 to 80 weight percent of copper oxide and 20 to 40 weight percent of zinc oxide.

3. A process according to claim 1 wherein the molar ratio of hydrogen to anhydride in the vaporous mixture of the hydrogen containing gas and the maleic anhydride and/or succinic anhydride is between 10 to 1 and 300 to 1.

4. The process according to claim 3 wherein the hydrogenation is conducted at a temperature of about 150° to 350° C.

5. The process according to claim 4 wherein the hydrogenation is conducted at a pressure of about 1 to 100 bar.

6. The process according to claim 1 wherein the hydrogenation is conducted at a temperature of about 150° to 350° C.

7. The process according to claim 1 wherein the hydrogenation is conducted at a pressure of about 1 to 100 bar.

8. The process according to claim 1 wherein the molar ratio of hydrogen to anhydride in the vaporous mixture of the hydrogen containing gas and the maleic anhydride and/or succinic anhydride is between 40:1 and 200:1.

9. The process according to claim 3 wherein the hydrogen containing gas is hydrogen.

10. The process according to claim 1 wherein the hydrogenation is continuously conducted in a tubular reactor.

11. A process for the production of gamma-butyrolactone consisting essentially of catalytically hydrogenating at least one member selected from the group consisting of maleic anhydride and succinic anhydride, in a vaporous mixture with a hydrogen containing gas with a catalyst comprising a catalytically active oxide material comprising a mixed oxide of 50 to 90 weight percent of copper oxide and 10 to 50 weight percent of zinc oxide, with the proviso that aluminum oxide is excluded from said catalytically active material, on an inert support.

12. The process according to claim 11 wherein the inert support is composed of a material selected from the group consisting of silica, silica-alumina compound, silica carbide, steatite and titania.

13. The process according to claim 11 wherein said mixed oxide consists essentially of 60 to 80 weight percent copper oxide and 20 to 40 weight percent zinc oxide.

14. The process according to claim 11 wherein the molar ratio of hydrogen to anhydride in the vaporous mixture of the hydrogen containing gas and the maleic anhydride and/or succinic anhydride is between 10 to 1 and 300 to 1.

15. The process according to claim 11 wherein the molar ratio of hydrogen to anhydride in the vaporous mixture of the hydrogen containing gas and the maleic anhydride and/or succinic anhydride is between 40:1 and 200:1.

16. The process according to claim 11 wherein the hydrogen containing gas is hydrogen.

17. The process according to claim 11 wherein the hydrogenation is continuously conducted.

18. The process according to claim 13 wherein the hydrogenation is conducted at a temperature of about 150° and 350° C.

19. The process according to claim 18 wherein the hydrogenation is conducted at a pressure of about 1 to 100 bar.

20. A process for the production of gamma-butyrolactone consisting essentially of catalytically hydrogenating at least one member selected from the group consisting of maleic anhydride and succinic anhydride, in a vaporous mixture with a hydrogen containing gas with catalyst composed of catalytically active oxide material comprising a mixed oxide of 50 to 90 weight percent copper oxide and 10 to 50 weight percent of zinc oxide, the molar ratio of hydrogen to anhydride in the vaporous mixture of the hydrogen containing gas and the maleic anhydride and/or succinic anhydride is between 40:1 and 200:1.

21. The process according to claim 20 wherein the hydrogen containing gas is hydrogen.

22. The process according to claim 11 wherein the catalytically active oxide material is arranged between two layers of inert support material.

23. The process according to claim 11 wherein the catalytically active oxide material also contains an inert tabletting aid and/or an inert filler.

24. The process according to claim 11 wherein said mixed oxide is composed of 60 to 80 weight percent of copper oxide and 20 to 40 weight percent of zinc oxide.

25. The process according to claim 24 wherein the hydrogenation is conducted at a temperature of about 150° and 350° C.

26. The process according to claim 25 wherein the hydrogenation is conducted at a pressure of about 1 to 100 bar.

27. The process according to claim 11 wherein the hydrogenation is conducted at a temperature of about 150° to 350° C.

28. The process according to claim 11 wherein the hydrogenation is conducted at a pressure of about 1 to 100 bar.

* * * * *